United States Patent [19]

Blunck

[11] 4,004,146
[45] Jan. 18, 1977

[54] INFRARED GAS ANALYZING PHOTOMETER WITH CHOPPER DESIGNED TO AVOID RADIATION WASTE

[75] Inventor: Otto Blunck, Hamburg, Germany
[73] Assignee: H. Maihak A.G., Hamburg, Germany
[22] Filed: Apr. 15, 1975
[21] Appl. No.: 568,246
[52] U.S. Cl. .............................. 250/345; 250/233; 250/347; 250/351; 350/274; 356/51
[51] Int. Cl.² .................. G01N 21/34; G01D 5/36
[58] Field of Search ................ 356/51, 93, 95, 188; 250/340, 345, 347, 351, 353, 575, 230, 233; 350/273, 274, 275

[56] References Cited
UNITED STATES PATENTS

| | | | |
|---|---|---|---|
| 3,588,496 | 6/1971 | Snowman | 356/51 |
| 3,669,547 | 6/1972 | Sell | 356/93 |
| 3,749,497 | 7/1973 | Kuzmin | 356/93 |
| 3,899,252 | 8/1975 | Dimeff | 356/51 |

Primary Examiner—Vincent P. McGraw
Attorney, Agent, or Firm—Michael J. Striker

[57] ABSTRACT

An infrared gas analyzer is provided with a first path for reference radiation and a second path for measuring radiation. A source emits infrared radiation into the first and second paths. A detector arrangement is positioned at the ends of the paths for sensing the intensity of reference and measuring radiation passing through the paths. A radiation-travel-control arrangement alternately blocks one and then the other of the two paths and during the blocking of each path causes radiation directed towards the blocked path to be deflected into the unblocked path so that such radiation is not wasted.

15 Claims, 1 Drawing Figure

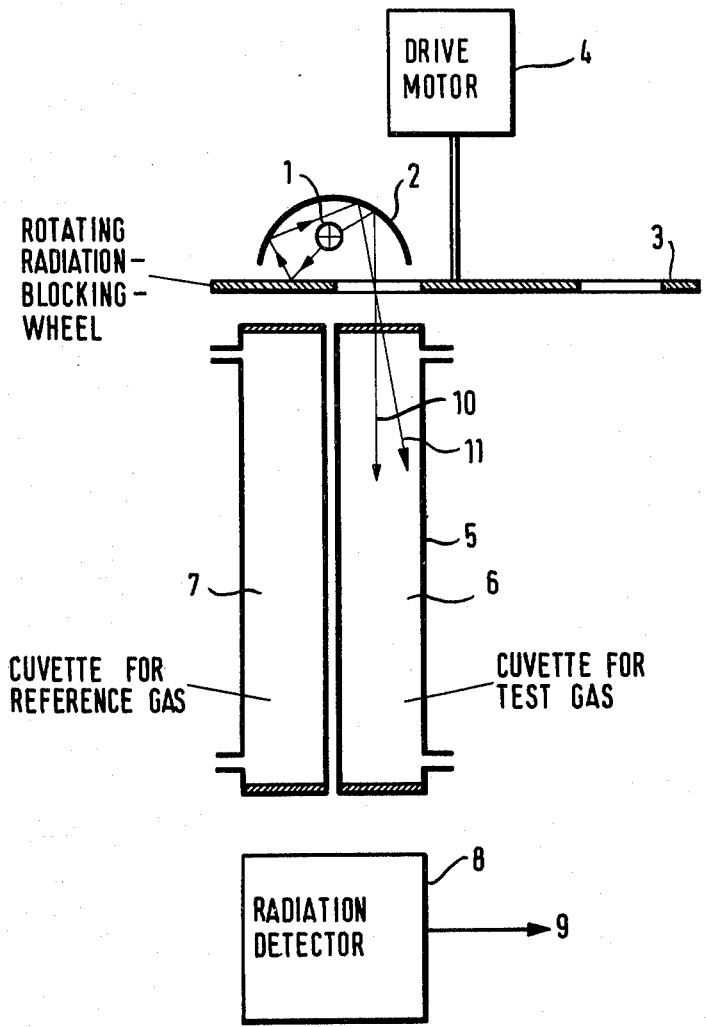

INFRARED GAS ANALYZING PHOTOMETER WITH CHOPPER DESIGNED TO AVOID RADIATION WASTE

BACKGROUND OF THE INVENTION

The invention relates to gas analyzing infrared photometer arrangements of the type in which there are provided a first path for reference radiation and a second path for measuring radiation. These paths are usually the paths of radiation through respective first and second cuvettes filled with a reference sample and a test sample of a gas to be analyzed. More particularly, the invention relates to arrangements of this type wherein infrared radiation is emitted towards the entrances of both paths, but wherein some means are provided for alternately blocking one and then the other of the two paths.

Brochure No. 1557/9 issued by the firm H. Maihak AG of West Germany discloses one such infrared gas analyzer. This analyzer makes use of a radiation-blocking wheel located intermediate the radiation source and the two radiation paths. The blocking wheel has angularly offset portions which respectively block and transmit radiation, and the wheel is rotated so as to alternately block one and then the other of the two radiation paths. Thus there is an alternation between passage of infrared radiation through the cuvette containing the test sample of gas and passage of infrared radiation through the cuvette containing the reference gas sample. The blocking wheel, on the side thereof facing the radiation source, is not provided at the blocking portion or portions thereof with any means for handling the radiation incident upon such blocking portion or portions. Accordingly, when a blocking portion of the blocking wheel blocks one of the two radiation passages, the radiation incident upon such blocking portion is not utilized; half the emitted radiation passes through the unblocked cuvette, whereas the other half is absorbed by the blocking portion of the blocking wheel. Accordingly, the utilization efficiency of the useful radiated energy is only about 50%.

German published patent application DT-OS No. 1,948,193 discloses another infrared gas analyzer. This arrangement includes a source of infrared radiation, a first path for measuring radiation and a second path for reference radiation, a detector for sensing the radiation passing through the paths, and a mirrored radiation-blocking wheel which is rotated so as to alternately block one and then the other of the two radiation paths. Specifically, the radiation emitted by the source is permitted to pass through both radiation paths (e.g., cuvettes) simultaneously, not merely alternately. The radiation emerging from each path is incident upon a respective one of two deflecting mirrors. The mirrored light-blocking wheel is positioned intermediate the two deflecting mirrors. The light-blocking wheel is rotatable between a first position and a second position. In the first position, it receives the light from one of the deflecting mirrors and reflects such light towards the detector; at the same time, it blocks the light reflected from the other deflecting mirror so that such light cannot reach the detector. In the second position, without further reflection it transmits to the detector the light from the one deflecting mirror, while not reflecting towards the detector the light from the other deflecting mirror. With this arrangement, likewise, only about 50% of the useful radiation is used during any one light measurement; the remaining 50% of the useful radiation is simply absorbed by the light-blocking wheel.

Finally, German allowed patent application DT-AS 1,123,139 discloses a third infrared-absorption gas analyzer. In that construction, there are associated with the source two planar deflecting mirrors, forming an angle of about 90° with each other, and located on opposite sides of the source. Accordingly, two distinct radiation paths are established. Radiation travelling along these two paths is first incident upon a radiation-blocking wheel located intermediate the source and deflecting mirrors, on the one hand, and the reference and measuring cuvettes, on the other hand. With this known construction, there is essentially no possibility of utilizing that part of the emitted radiation which is incident upon the blocking portion of the radiation-blocking wheel.

SUMMARY OF THE INVENTION

It is a main object of the invention to greatly increase the efficiency with which the radiation emitted in photometers of the type in question is utilized, so as to be able to increase the intensity of the radiation available for the absorption process.

This object, and others which will become more understandable from the following description of an exemplary embodiment, can be met, according to one advantageous concept of the invention, by providing, in an infrared gas analyzer, in combination, means defining a first path for reference radiation and a second path for measuring radiation; radiating means operative for emitting radiation into said paths; detector means positioned at the ends of said paths for sensing the intensity of reference and measuring radiation passing through said paths; and radiation-travel-control means operative for alternately blocking one and then the other of said paths and during the blocking of each path causing radiation directed towards the blocked path to be deflected into the unblocked path so that such radiation is not wasted.

In the exemplary embodiment disclosed herein, the radiation source emits radiation both towards the two light paths and away therefrom, and so there is arranged back of the source a reflector for reflecting the light directed away from paths towards the paths. In the exemplary embodiment, the radiation-blocking wheel has a mirrored surface on the side thereof facing the radiation source. Accordingly, radiation emitted from the source and the cooperating reflector towards the blocked light path is reflected by the mirrored surface on the blocking wheel back towards the reflector and from there into the unblocked light path.

In this way, it becomes possible to make available for the absorption process practically the entire radiation emitted from the radiation source, so that either the output power or radiation intensity of the source can be advantageously decreased, or so that during the absorption process use can be made of radiation having a markedly higher intensity.

It is particularly advantageous if the side of the light-blocking member facing the radiation source is provided with a layer of reflective material. This makes possible a simple and advantageous manufacture of the light-blocking member.

This layer of reflective material can be provided on the light-blocking member either by vapor deposition or by anodic electrodeposition. Both possibilities are characterized by reflection of high quality and by low weight for the mirrored light-blocking member.

The provision of a mirrored surface on the light-blocking member can also be accomplished by cementing onto the back surface of the member a reflective foil. Since this expedient involves little technical complexity, it constitutes a particularly good way of producing the light-blocking member.

It is also considered advantageous to provide the reflective layer upon an electrolytically oxidized aluminum layer. This layer constitutes a tight and fast-holding protective layer which, on account of its low density, increases the mass and accordingly the moment of inertia of the light-blocking member only negligibly. Onto this layer the reflective layer is deposited, mounted or otherwise provided. This has the advantage that the reflective layer firmly holds to the electrolytically oxidized aluminum layer, avoiding the possibility that portions of the reflective layer might flake off and dirty the window of the optical radiation guide.

For the reflective layer itself, particularly suitable are those materials which have a higher reflective efficiency in the infrared region of the spectrum, such as for example gold, silver or the like. In actual practice, using vapor-deposited gold for the reflective layer on the light-blocking disk, there is achieved an efficiency increase of 30% relative to non-mirrored blocking members.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

The single FIGURE schematically depicts one exemplary version of an infrared gas analyzer according to the invention.

DESCRIPTION OF THE PREFERRED EMBODIMENTS

Referring to the FIGURE, reference numeral 1 denotes a source of infrared radiation. Reference numeral 2 denotes a cooperating reflector which receives the radiation emitted by the source 1 in upwards direction (as viewed in the FIGURE) and reflects such radiation downwardly. Reference numeral 3 denotes a light-blocking wheel 3 driven by a drive motor 4. The radiation emitted by the radiating means 1, 2 is split up into two phase-opposed modulated radiation components both of which pass through the measuring arrangement 5, but in such a manner that one radiation component passes through the analysis cuvette 6 for the gas sample to be studied whereas the other radiation component passes through the reference cuvette 7 containing the reference gas sample. The two radiation components after passing through the respective cuvettes impinge upon a radiation detector 8 which generates an output signal 9 which is further processed in a manner not requiring description.

The radiation-blocking wheel 3, on the side thereof facing the radiating means 1, 2, is mirrored, so that for example the radiation 11 reflected off the mirrored back surface of the wheel 3 is deflected into and passes through the unblocked radiation path of cuvette 6, in addition to the radiation 10 which the radiating means 1, 2 emits directly towards the radiation path of cuvette 6. The radiation reflected off the mirrored surface of blocking wheel 3 would, in the prior-art arrangements, simply be absorbed by the non-reflective material of the blocking portion of the blocking wheel. As a result, with the arrangement shown in the FIGURE, the effective intensity of the radiation employed is increased. The side of the radiation-blocking wheel 3 which faces the cuvettes 6, 7 is not mirrored, in order to prevent radiation from being reflected from within one cuvette into the interior of the other cuvette, which would lead to a reduction of the output signal amplitude.

In operation, the drive 4 rotates the radiation-blocking wheel 3 and causes alternate blocking of the radiation path of cuvette 6 and of cuvette 7. The blocking or obstructing of one and then the other path, alternately, is effected by interposing into one and then the other path, alternately, material which does not transmit the radiation in question. When the blocking wheel 3 assumes the position thereof in which the radiation path of cuvette 6 is blocked and that of cuvette 7 is unblocked, the radiation emitted by radiating means 1, 2 directly towards the radiation path of cuvette 6 will be reflected by the mirrored upper surface of wheel 3 and deflected into the radiation path of cuvette 7.

The mirrored radiation-blocking wheel 3 can be provided with a single pair of radiation-transmitting portions angularly offset from each other, considered with respect to the rotation axis of the wheel 3, or can be provided with a plurality of such angularly spaced radiation-transmitting portions. The transmitting-portions can be apertures or portions of transmissive material.

In exemplary embodiment described above, use is made of a rotating radiation-blocking disk. However, it would also be possible to use a reciprocating radiation-blocking member, or a plurality of cooperating and synchronized radiation-blocking members, for example two rotating blocking disks operating in phase opposition, two reciprocating radiation-blocking strips, or the like. However, the exemplary embodiment is preferred because of its simplicity.

Also, in the exemplarly embodiment, radiation directed towards the blocked light path is deflected into the unblocked path, so as not to be wasted, using the reflecting surfaces of members 3 and 2. However, a different number of radiation-deflecting surfaces could be employed.

It will be understood that each of the elements described above, or two or more together, may also find a useful application in other types of constructions differing from the types described above.

While the invention has been illustrated and described as embodied in a gas analyzing infrared photometer, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. In an infrared gas analyzer, in combination, means defining a first path for reference radiation and a second path for measuring radiation; radiating means operative for emitting radiation towards both said paths simultaneously; detector means positioned at the ends of said paths for sensing the intensity of reference and measuring radiation passing through said paths; and radiation-travel-control means operative for alternately obstructing by the interposition of material which does not transmit the emitted radiation one and then the other of said paths and during the obstructing of each path causing the radiation directed towards the obstructed path to be deflected into the unobstructed path so that such radiation is not wasted.

2. In an analyzer as defined in claim 1, wherein said radiation-travel-control means comprises means operative for alternately obstructing one and then the other of said paths and during the obstructing of each path causing the radiation directed towards the obstructed path to be reflected into the unobstructed path.

3. In an analyzer as defined in claim 1, wherein said radiation-travel-control means comprises means operative during the obstructing of each path for causing the radiation directed towards the obstructed path to be reflected back towards said radiating means and then reflected away from said radiating means and into the unobstructed path.

4. In an analyzer as defined in claim 1, wherein said radiation-travel-control means comprises means operative during the obstructing of each path for causing the radiation directed towards the obstructed path to be reflected back towards said radiating means and then deflected away from said radiating means and into the unobstructed path, and including at least one obstructing member located intermediate said radiating means and said paths, said obstructing member on the side thereof facing said radiating means being at least partially mirrored, and said obstructing member being mounted for movement between a first position in which it obstructs said first path and reflects back towards said radiating means radiation directed towards said first path and a second position in which it obstructs said second path and reflects back towards said radiating means radiation directed towards said second path, and moving means connected to said obstructing member for causing the latter to alternate between said first position and said second position.

5. In an analyzer as defined in claim 1, wherein said radiating means comprises a radiation source which emits infrared radiation both in direction towards said paths and in direction away from said paths and a cooperating reflector for reflecting into said paths infrared radiation which is emitted from said source in direction away from said paths.

6. In an analyzer as defined in claim 5, wherein said radiation-travel-control means comprises means operative for alternately obstructing one and then the other of said paths and during the obstructing of each path causing the radiation directed towards the obstructed path to be reflected back towards said reflector of said radiating means and reflected from the latter into the unobstructed path.

7. In an analyzer as defined in claim 5, wherein said radiation-travel-control means comprises means operative during the obstructing of each path for causing the radiation directed towards the obstructed path to be deflected back towards said reflector of said radiating means and reflecting from the latter into the unobstructed path.

8. In an analyzer as defined in claim 7, wherein said radiation-travel-control means comprises at least one obstructing member located intermediate said radiating means and said paths, said obstructing member on the side thereof facing said radiating means being at least partially mirrored, and said obstructing member being mounted for movement between a first position in which it obstructs said first path and reflects radiation directed towards said first path back to said reflector and a second position in which it obstructs said second path and reflects radiation directed towards said second path back to said reflector, and moving means connected to said obstructing member for causing the latter to alternate between said first position and said second position.

9. In an analyzer as defined in claim 4, wherein said obstructing member is provided on the side thereof facing said radiating means with a layer of reflective material.

10. In an analyzer as defined in claim 9, wherein said layer is a vapor-deposited layer.

11. In an analyzer as defined in claim 9, wherein said layer is an anodically electrodeposited layer.

12. In an analyzer as defined in claim 9, wherein said layer is a reflective foil cemented onto said side of said obstructing member.

13. In an analyzer as defined in claim 9, wherein said layer of reflective material is provided on an electrolytically oxidized layer of aluminum.

14. In an analyzer as defined in claim 9, wherein said layer of reflective material is of high reflective efficiency in the infrared portion of the light spectrum.

15. In an infrared gas analyzer, in combination, means defining a first path for reference radiation and a second path for measuring radiation; radiating means operative for emitting radiation into said paths; detector means positioned at the ends of said paths for sensing the intensity of reference and measuring radiation passing through said paths; and radiation-travel-control means operative for alternately blocking one and then the other of said paths and during the the blocking of each path causing the radiation directed towards the blocked path to be deflected into the unblocked path so that such radiation is not wasted, wherein said radiating means comprises a radiation source emitting infrared radiation both towards and away from said paths and a cooperating reflector behind said source for reflecting into said paths infrared radiation emitted from said source in direction away from said paths, wherein said radiation-travel-control means comprises means operative for alternately blocking one and then the other of said paths and during the blocking of each path causing the radiation directed towards the blocked path to be reflected back towards said reflector and reflected from the latter into the unblocked path, including a blocking wheel located between said radiating means and said paths immediately in front of said radiating means, said wheel having at least one radiation-blocking portion and at least one radiation-transmitting portion, said wheel on the side thereof facing said radiating means being at least partially mirrored at said blocking portion thereof, said wheel being mounted for rotation between a first position in which it blocks said first path and reflects radiation directed towards said first path back to said reflector and a second position in which it blocks said second path and reflects radiation directed towards said second path back to said reflector and drive means connected to said wheel for causing the latter to rotate.

* * * * *